United States Patent [19]

Moore

[11] Patent Number: 6,153,791
[45] Date of Patent: Nov. 28, 2000

[54] PROCESS FOR PURIFYING 2-KETO-L-GULONIC ACID

[75] Inventor: Kevin M. Moore, Mt. Zion, Ill.

[73] Assignee: Archer-Daniels-Midland Company, Decatur, Ill.

[21] Appl. No.: 09/366,279

[22] Filed: Aug. 2, 1999

[51] Int. Cl.$^7$ .......................... C07C 51/42; C07C 59/105
[52] U.S. Cl. .......................................... 562/513; 562/577
[58] Field of Search ................................ 562/513, 577

[56] References Cited

U.S. PATENT DOCUMENTS

| | | | |
|---|---|---|---|
| 2,223,797 | 12/1940 | Trindall | 260/535 |
| 2,421,611 | 6/1947 | Gray | 195/47 |
| 2,539,472 | 1/1951 | Ratchford et al. | 260/535 |
| 2,650,248 | 8/1953 | Collier | 260/537 |
| 2,664,441 | 12/1953 | Owens et al. | 260/527 |
| 2,697,724 | 12/1954 | Collier | 260/527 |
| 2,710,880 | 6/1955 | Filachione et al. | 260/535 |
| 3,086,928 | 4/1963 | Schulz | 204/72 |
| 3,234,105 | 2/1966 | Motizuki et al. | 195/49 |
| 3,531,463 | 9/1970 | Gustafson | 260/211.5 |
| 3,780,097 | 12/1973 | Doss et al. | 260/525 |
| 3,907,639 | 9/1975 | Makover et al. | 195/36 |
| 3,912,592 | 10/1975 | Makover et al. | 195/31 |
| 3,944,606 | 3/1976 | Rieger et al. | 260/535 |
| 4,250,331 | 2/1981 | Shimshick | 562/485 |
| 4,275,234 | 6/1981 | Baniel et al. | 562/584 |
| 4,282,323 | 8/1981 | Yates | 435/140 |
| 4,308,398 | 12/1981 | Borchert | 562/584 |
| 4,323,702 | 4/1982 | Kawabata et al. | 562/485 |
| 4,334,095 | 6/1982 | Baniel | 562/584 |
| 4,405,717 | 9/1983 | Urbas | 435/140 |
| 4,444,881 | 4/1984 | Urbas | 435/139 |
| 4,522,726 | 6/1985 | Berry et al. | 210/660 |
| 4,698,303 | 10/1987 | Bailey et al. | 435/139 |
| 4,705,894 | 11/1987 | Su et al. | 562/580 |
| 4,724,262 | 2/1988 | Shimbo et al. | 549/222 |
| 4,764,276 | 8/1988 | Berry et al. | 210/264 |
| 4,808,317 | 2/1989 | Berry et al. | 210/660 |
| 4,874,700 | 10/1989 | Seipenbusch | 435/145 |
| 4,877,735 | 10/1989 | Nogami et al. | 435/138 |
| 4,879,412 | 11/1989 | Iwasaki et al. | 562/600 |
| 4,892,823 | 1/1990 | Imai et al. | 435/138 |
| 4,902,828 | 2/1990 | Wickenhaeuser et al. | 562/577 |
| 4,933,289 | 6/1990 | Imai et al. | 435/253.3 |
| 4,935,359 | 6/1990 | Yin et al. | 435/138 |
| 4,960,695 | 10/1990 | Hoshino et al. | 435/42 |
| 4,990,441 | 2/1991 | Barthole et al. | 435/138 |
| 4,994,609 | 2/1991 | Baniel et al. | 562/580 |
| 5,032,686 | 7/1991 | Duflot et al. | 562/580 |
| 5,041,645 | 8/1991 | Alon et al. | 562/584 |
| 5,069,883 | 12/1991 | Matonte | 422/269 |
| 5,089,664 | 2/1992 | Dalcanale et al. | 562/580 |
| 5,132,456 | 7/1992 | King et al. | 562/593 |
| 5,194,130 | 3/1993 | Byszewski et al. | 204/182.4 |
| 5,202,476 | 4/1993 | Tsuda et al. | 562/513 |
| 5,210,294 | 5/1993 | Mantovani et al. | 562/580 |
| 5,210,296 | 5/1993 | Cockrem et al. | 562/589 |
| 5,231,225 | 7/1993 | Baniel et al. | 562/513 |
| 5,237,098 | 8/1993 | Bemish et al. | 562/584 |
| 5,278,339 | 1/1994 | Cook | 562/509 |
| 5,312,741 | 5/1994 | Hoshino et al. | 435/42 |
| 5,391,770 | 2/1995 | Le Fur | 549/315 |
| 5,391,771 | 2/1995 | Weyer et al. | 549/326 |
| 5,426,219 | 6/1995 | Lehnhardt et al. | 562/580 |
| 5,510,526 | 4/1996 | Baniel et al. | 562/580 |
| 5,522,995 | 6/1996 | Cockrem | 210/637 |

FOREIGN PATENT DOCUMENTS

| | | |
|---|---|---|
| 0 805 210 A2 | 11/1997 | European Pat. Off. . |
| 0 805 210 A3 | 7/1999 | European Pat. Off. . |
| 55-124735 | 9/1980 | Japan . |
| 2-121947 | 5/1990 | Japan . |
| 2-121948 | 5/1990 | Japan . |
| 4-320691 | 11/1992 | Japan . |
| WO 92/16490 | 10/1992 | WIPO . |
| WO 97/13569 | 4/1997 | WIPO . |

OTHER PUBLICATIONS

Manual, Advanced Separation Technologies, Inc., pp. 1a, 1b, 1c, 1d, 2a, 2b, 3–9a, 9b–9g, 10–24a, 24b and 24c (1996).

Reichstein, T., and Grüssner, A., "Eine ergiebige Synthese der 1–Ascorbinsäure (C–Vitamin)," *Helvetica Chimica Acta* 17:311–328 (1934).

Derwent WPI Database (English Translation) for JP 2–121947, printed Nov. 12, 1999, pp. 1–2.

Derwent WPI Database (English Translation) for JP 2–121948, printed Nov. 12, 1999, p. 1.

Derwent WPI Database (English Translation) for EP 0 805 210 A2, printed Nov. 12, 1999, pp. 1–2.

Patent Abstracts of Japan (English translation) for JP 55–124735, printed Nov. 2, 1999, pp. 1–2.

Patent Abstracts of Japan (English translation) for JP 4–320691, printed Nov. 2, 1999, pp. 1–2.

*Primary Examiner*—Johann Richter
*Assistant Examiner*—Brian J. Davis
*Attorney, Agent, or Firm*—Sterne, Kessler, Goldstein & Fox P.L.L.C.

[57] ABSTRACT

The present invention relates to a process for the purification of 2-keto-L-gulonic acid by continuous liquid chromatography using a weakly basic ion exchange resin.

18 Claims, 4 Drawing Sheets

PROCESS FOR PURIFYING 2-KETO-L-GULONIC ACID

FIELD OF THE INVENTION

The present invention relates to a process for the purification of 2-keto-L-gulonic acid by continuous liquid chromatography using a weakly basic ion exchange resin.

BACKGROUND OF THE INVENTION

2-Keto-L-gulonic acid is a significant intermediate in the preparation of L-ascorbic acid (vitamin C), an essential nutrient. While 2-keto-L-gulonic acid has been synthesized in the past on an industrial scale using the Reichstein method (*Helvetica Chimica Acta* 17:311 (1934)), fermentation processes employing one or more microorganisms are preferred for commercial production of 2-keto-L-gulonic acid. U.S. Pat. No. 2,421,611, for example, discloses a method involving microbial oxidation of D-glucose to 5-keto-D-gluconic acid, followed by chemical or microbial reduction to L-idonic acid and subsequent microbial oxidation to 2-keto-L-gulonic acid. Japanese Patent Publication Nos. 39-14493, 53-25033, 56-15877 and 59-35290, for example, disclose similar processes involving the microbial oxidation of D-glucose to 2,5-diketo-D-gulonic acid followed by microbial or chemical reduction to 2-keto-L-gulonic acid. Fermentative pathways involving oxidation of L-sorbose to 2-keto-L-gulonic acid via a sorbosone intermediate have also been developed, using *Gluconobacter oxydans* (U.S. Pat. Nos. 4,935,359; 4,960,695; and 5,312,741), *Pseudogluconobacter saccharoketogenes* (U.S. Pat. No. 4,877,735), *Pseudomonas sorbosoxidans* (U.S. Pat. Nos. 4,933,289 and 4,892,823), and mixtures of microorganisms (U.S. Pat. Nos. 3,912,592; 3,907,639; and 3,234,105).

Prior to conversion into ascorbic acid, however, 2-keto-L-gulonic acid must first be isolated from the fermentation broth. As described in U.S. Pat. No. 4,990,441, for example, 2-keto-L-gulonic acid can be recovered from a fermentation broth by a process comprising the steps of: (a) removing insoluble material from the broth by centrifugation, filtration in the presence of a flocculating agent, or ultrafiltration; (b) removing inorganic cations by acidification; and (c) isolating 2-keto-L-gulonic acid by crystallization. High yields of 2-keto-L-gulonic acid are difficult to obtain by this method, however, due to the high solubility of 2-keto-L-gulonic acid in the crystallization mother liquor.

Moreover, conversion to ascorbic acid according to the method described in U.S. Pat. No. 5,391,771 includes preparation of the methyl ester of 2-keto-L-gulonic acid by reaction with methanol. This esterification reaction involves an equilibrium between the free acid form and methyl ester of 2-keto-L-gulonic acid and so requires substantially anhydrous conditions to ensure sufficient yields of the desired product for commercial application.

Accordingly, there remains a need for a process for recovering 2-keto-L-gulonic acid from aqueous solutions, such as fermentation broths, in high yields.

Processes for removal of acids from aqueous media have been developed employing anionic ion exchange resins. Such processes are described, for example, in U.S. Pat. Nos. 5,278,339 (cyclohexanedicarboxylic acids) and 4,323,702 (carboxylic acids such as adipic acid) and in International Publication No. WO 92/16490 (citric acid). In all of these processes, the acid of interest is first adsorbed onto an anionic resin to a maximum value (as determined by measuring the change in the concentration of acid in the effluent during loading) and then subsequently desorbed with an agent that regenerates the anionic resin. These processes are generally not, however, suitable for recovering 2-keto-L-gulonic acid from aqueous solutions because the water content of the recovered 2-keto-L-gulonic acid tends to be too high for subsequent esterification without additional purification steps.

Accordingly, there remains a need for a process for recovering 2-keto-L-gulonic acid from aqueous solutions, such as fermentation broths, substantially water-free.

SUMMARY OF THE INVENTION

It is therefore an object of the present invention to provide methods of purifying 2-keto-L-gulonic acid in high yields. Other objects, features and advantages of the present invention will be set forth in the detailed description of preferred embodiments that follows, and in part will be apparent from the description or may be learned by practice of the invention. These objects and advantages of the invention will be realized and attained by the methods particularly pointed out in the written description and claims hereof.

These and other objects are accomplished by the methods of the present invention, which, in a first embodiment, is broadly directed to a process for the purification of 2-keto-L-gulonic acid by a continuous chromatographic process using a weakly basic ion exchange resin. Other preferred embodiments of the present invention will be described in more detail below.

It is to be understood that both the foregoing general description and the following detailed description are exemplary and explanatory only and are intended to provide further explanation of the invention as claimed.

DETAILED DESCRIPTION OF PREFERRED EMBODIMENTS OF THE INVENTION

Figure 1:
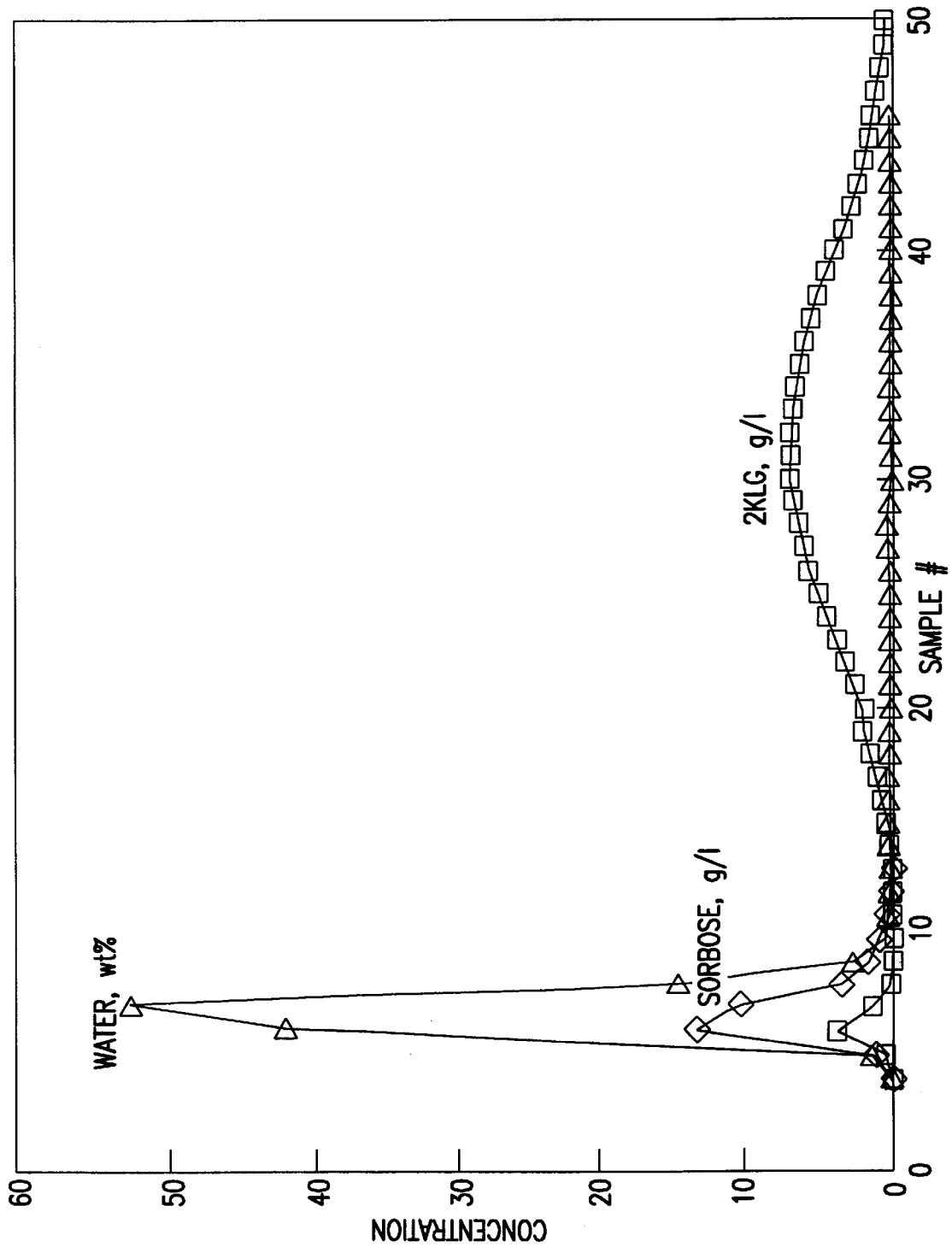
FIG. 1 is a graph showing the purification of 2-keto-L-gulonic acid as described in EXAMPLE 1.

In a first preferred embodiment, the present invention is directed to a process for the purification of 2-keto-L-gulonic acid using a continuous chromatography system having a plurality of chambers. Each chamber of the plurality of chambers contains solid particulate matter and has an inlet for permitting fluid to enter the chamber and an outlet for permitting fluid to exit the chamber.

The inventive process preferably comprises the following steps of:

(a) introducing an aqueous solution containing 2-keto-L-gulonic acid into one of the plurality of chambers through the inlet of that chamber such that the aqueous solution contacts the solid particulate material contained in the chamber and then exits the chamber through its outlet;

(b) introducing a solvent into the chamber through its inlet in the same fashion as the aqueous solution in step (a) (i.e. such that the aqueous solution contacts the solid particulate material contained in the chamber and then exits through its outlet);

(c) conducting the aqueous solution exiting the chamber through its outlet to a second chamber;

(d) collecting the solvent exiting the chamber through its outlet;

(e) introducing the aqueous solution into the second chamber through its inlet in the same fashion as for the first chamber (i.e. such that the aqueous solution contacts the solid particulate material contained in the chamber and then exits through its outlet); and (f) repeating steps (b)–(e) for each chamber of the plurality of chambers.

In an alternative embodiment, the solvent is not collected in step (d), but is instead introduced directly into the second chamber of the plurality of chambers through its inlet following step (f). According to this alternative embodiment of the inventive process, the solvent is collected after it has exited the last of the plurality of chambers, i.e. after steps (b)–(e) have been completed for all chambers of the plurality of chambers, or at the conclusion of any intermediate cycle, i.e. after steps (b)–(e) have been completed for a fixed number of the plurality of chambers, rather than after steps (b)–(e) have been completed for each chamber.

After the solvent containing 2-keto-L-gulonic acid has been collected, 2-keto-L-gulonic acid may be isolated and recovered according to conventional methods.

The solvent employed in the inventive process may be any solvent which allows for the selective purification of 2-keto-L-gulonic acid from the aqueous solution. Suitable solvents may be determined empirically by those skilled in the art. Preferably, the solvent is water or a lower alcohol, such as methanol or ethanol.

In a particularly preferred embodiment of the inventive process, the solvent employed is chosen based in part on its suitability for use in the subsequent conversion of 2-keto-L-gulonic acid to ascorbic acid. For example, conversion of 2-keto-L-gulonic acid to ascorbic acid according to the method described in U.S. Pat. No. 5,391,771 includes preparation of the methyl ester of 2-keto-L-gulonic acid by reaction of the free acid with methanol. In such an embodiment of the inventive process, the solvent employed is preferably methanol, more preferably anhydrous methanol.

The aqueous solution of step (a) (i.e. the solution from which 2-ketoL-gulonic acid is being isolated) is typically, but not always, a fermentation broth produced by the cultivation of one or more microorganisms that produce 2-keto-L-gulonic acid and/or a precursor thereof. In addition to water, these fermentation broths generally contain the nutrients required by the microorganism(s) being employed to produce 2-keto-L-gulonic acid, including, but not limited to, amino acids, inorganic and/or organic salts, carbohydrates, and various vitamins and growth factors.

Preferably, the fermentation broth is first filtered to remove biomass and other insoluble impurities and/or treated with activated charcoal for color removal prior to step (a) of the inventive process. It has been found that recovery of 2-keto-L-gulonic acid is improved if the fermentation broth is filtered and/or treated with activated charcoal prior to step (a) of the inventive process above.

In addition to fermentation broths, 2-keto-L-gulonic acid may also be purified from any other aqueous solution containing 2-keto-L-gulonic acid using the process of the present invention.

Purification of 2-keto-L-gulonic acid according to the inventive process is improved when the 2-keto-L-gulonic acid is in the form of the free acid, rather than a salt. Accordingly, a substantial proportion of any cations that may be present in the aqueous solution containing 2-keto-L-gulonic acid (such as those employed for the control of pH during fermentation) are preferably removed from the aqueous solution prior to the chromatographic separation of the present invention.

The removal of cations from the aqueous solution may be accomplished using any of the methods and techniques known and available to those skilled in the art. Illustrative examples of suitable methods include precipitation of calcium ions using sulfuric acid and the use of strongly acidic cation exchange resins (in their hydrogen form).

The inventive process is preferably performed using a continuous chromatographic system, such as the ones described, for example, in U.S. Pat. No. 4,522,726; U.S. Pat. No. 4,764,276; U.S. Pat. No. 4,808,317; and U.S. Pat. No. 5,069,883. Illustrative examples of such systems are commercially available from Advanced Separation Technologies Inc. (Lakeland, Fla., USA).

The continuous chromatographic systems useful in performing the inventive process comprise a plurality of chambers, each having an inlet for fluid and an outlet for fluid. These systems are generally arranged and piped such that fluid exiting the outlet of one chamber of the plurality may be isolated (and collected) or may be introduced directly into the inlet of the next successive chamber of the plurality.

Each chamber of the system contains an appropriate amount of a solid particulate matter. The solid particulate matter is preferably a weakly basic ion exchange resin.

The particular weakly basic ion exchange resin employed as the solid particulate matter may be empirically selected from among the anionic resins known to those skilled in the art based on its affinity for 2-keto-L-gulonic acid, i.e., the resin should have sufficient selective affinity for 2-keto-L-gulonic acid to allow recovery of the desired amount and/or purity of 2-keto-L-gulonic acid from the aqueous solution containing it.

Preferably, the weakly basic ion exchange resin comprises an ion exchange resin having a pyridine functionality. More preferably, the weakly basic ion exchange resin is a polymer comprising vinylpyridine residues, such as poly 2-vinylpyridine or poly 4-vinylpyridine.

Suitable weakly basic ion exchange resins are preferably at least about 2% cross-linked, more preferably about 8%, with a suitable cross-linking agent, such as divinylbenzene. Illustrative examples of suitable ion exchange resins of this type include those in the REILLEX™ series (available from Reilley Industries, Indianapolis, Ind., USA), which are 2% or 25% cross-linked and exhibit good thermal stability.

In a particularly preferred embodiment of the present invention, the ion exchange resin is a poly 4-vinylpyridine resin, such as REILLEX™ HP.

A small amount of the pyridine groups involved may optionally be derivatized, such as to pyridine N-oxide or quaternary salt moieties, if desired, to modify the basicity of the resin as appropriate.

The ion exchange resin may be in any form known to those skilled in the art, such as beads or gels, and a particular form may be selected empirically. Preferably, the ion exchange resin is in the form of beads of a suitable size, such as 20 or 60 mesh.

The particular chromatographic conditions employed in the inventive process, such as the temperature and flow rate of the mobile phase(s) (i.e. the aqueous solution, the solvent, and, if optionally present, the ionic solution), may be determined empirically based on the desired yield and/or purity of the 2-keto-L-gulonic acid. The respective temperature and flow rate of each mobile phase may be independently determined and may be the same as or different from the temperature and/or flow rate of any other mobile phase(s).

In a particularly preferred embodiment of the present invention, the ion exchange capability of the solid particulate matter is regenerated after the solvent has exited the chamber. In such an embodiment, the inventive process further comprises the step of:

(d') introducing an ionic solution into the chamber through its inlet such that the ionic solution contacts the solid particulate material contained in the chamber and then exits the chamber through its outlet. This optional step is particularly preferred when employing the alternative embodiment of the inventive process described above, i.e. the inventive process in which the solvent is not collected after exiting each chamber but rather is introduced directly into the next successive chamber of the plurality of chambers.

Any ionic solution that regenerates the ion exchange capability of the solid particulate matter may be employed. Preferably, the ionic solution is a basic solution, more preferably a weakly basic solution, such as 1% sodium hydroxide.

The following examples are illustrative only and are not intended to limit the scope of the invention as defined by the appended claims. It will be apparent to those skilled in the art that various modifications and variations can be made in the methods of the present invention without departing from the spirit and scope of the invention. Thus, it is intended that the present invention cover the modifications and variations of this invention provided they come within the scope of the appended claims and their equivalents.

All patents and publications referred to herein are expressly incorporated by reference.

EXAMPLE 1

GENERATION OF FEED FOR PROCESS

A fermentation broth containing 70 g/L 2-keto-L-gulonic acid, 15 g/L sorbose (unconverted starting material) and 132 g/L total dry solids was employed. 26.6 L of broth was ultra filtered to remove biomass and other insoluble impurities, and after diafiltration 32.3 L of permeate was obtained (containing 55 g/L 2-keto-L-gulonic acid and 92 g/L total dry solids).

The permeate was passed over a strong cationic resin in the hydrogen form to convert any 2-keto-L-gulonic acid salts to the free acid, to give 58 L of 30 g/L 2-keto-L-gulonic acid with 96% removal of cations. The resulting solution was treated with activated charcoal to remove color and filtered. The solution was then evaporated to a 2-keto-L-gulonic acid concentration of 130 g/L, with 190 g/L total dry solids and 30 g/L sorbose.

EXAMPLE 2

2-KETO-L-GULONIC ACID PURIFICATION WITH METHANOL AT AMBIENT TEMPERATURE 70 mL of REILLEX™ HP resin (available from Reilley Industries, Indianapolis, Ind.) was loaded into a ½" diameter glass column. The resin was washed with 500 mL deionized water and then 500 mL anhydrous methanol. 10 mL of the solution prepared in EXAMPLE 1 was added to the top of the column. A pump, pulling from the bottom, was run at 3.0 mL/min. When the liquid sample level in the top of the column reached the top of the resin, methanol was allowed to enter the column. 9.0 mL samples were collected using an automated sample collector switching every 3 minutes. A total of 50 samples were collected and analyzed for 2-keto-L-gulonic acid, water, dry solids and sorbose.

The results are displayed in FIG. 1. As may be seen from the graph, water and sorbose were collected in samples 5–10, with about 4% 2-keto-L-gulonic acid, while 2-keto-L-gulonic acid was collected in samples 15–50, free of sorbose and with a water content of less than 0.5%. Recovery in samples 15–50 was 96% at a dry basis purity of 88%.

EXAMPLE 3

EFFECT OF TEMPERATURE ON PURIFICATION OF 2-KETO-L-GULONIC ACID USING METHANOL

Figure 2:
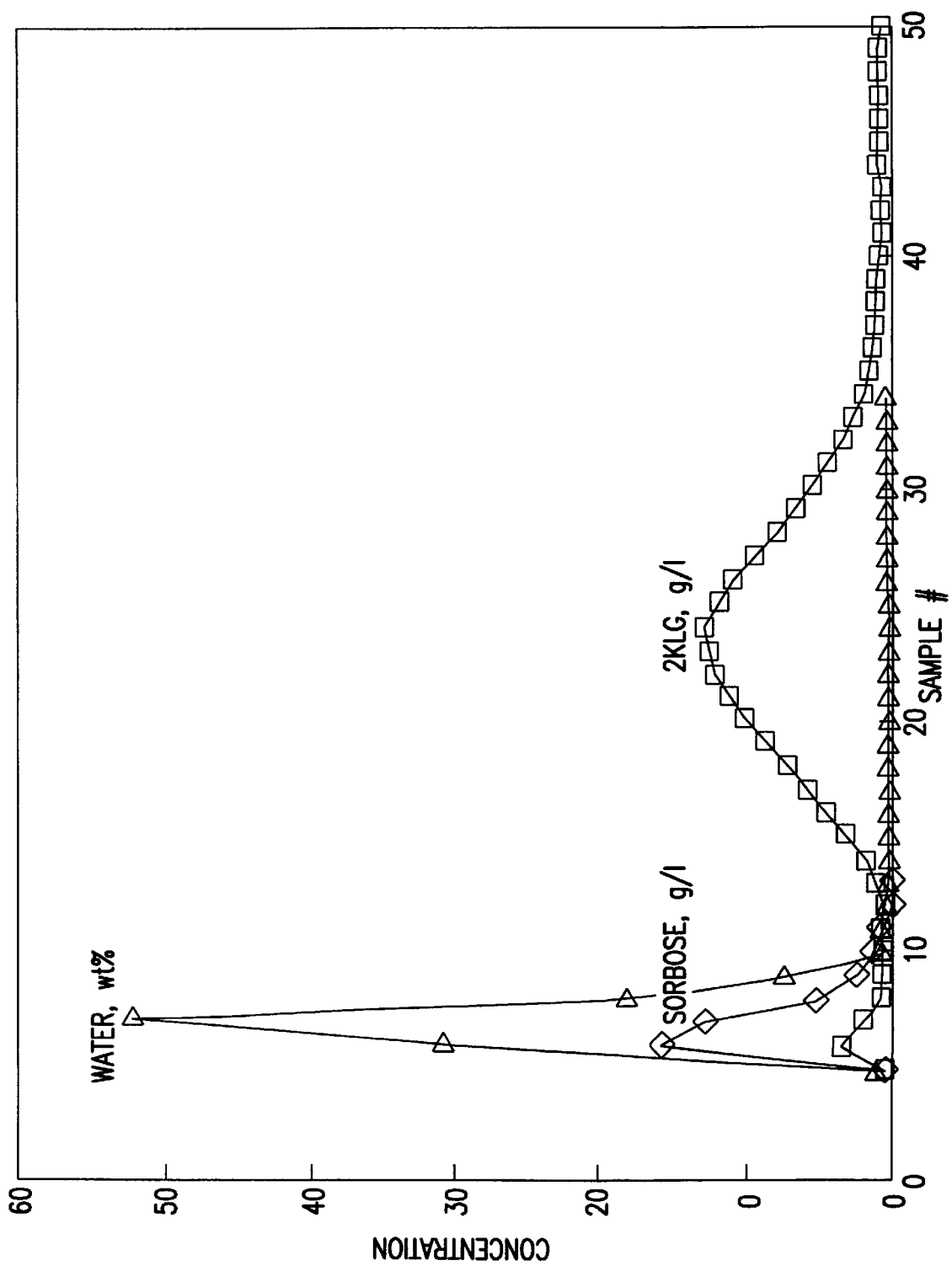
FIG. 2 is a graph showing the purification of 2-keto-L-gulonic acid as described in EXAMPLE 2.

EXAMPLE 2 was repeated, except that the temperature on the jacket of the column and the methanol feed was controlled at 50° C. The results are displayed in FIG. 2. Recovery of 2-keto-L-gulonic acid was 96%.

The data obtained from EXAMPLE 2 and EXAMPLE 3 suggest that, for recovery of 2-keto-L-gulonic acid with methanol, separation (and, concomitantly, purity) is best at ambient temperature while elution of higher 2-keto-L-gulonic acid concentrations occurs best at higher temperatures.

EXAMPLE 4

2-KETO-L-GULONIC ACID PURIFICATION WITH HOT WATER

Figure 3:
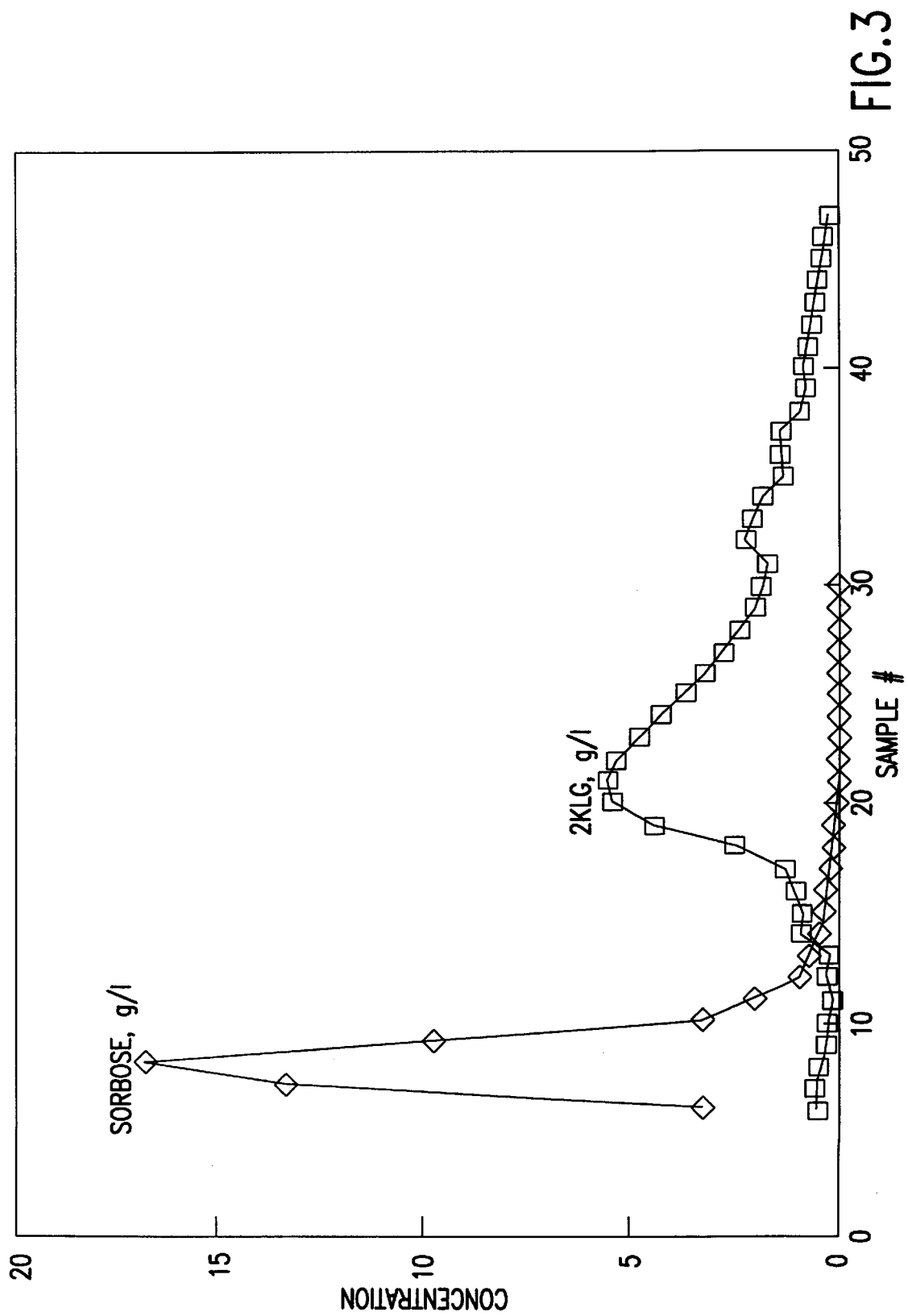
FIG. 3 is a graph showing the purification of 2-keto-L-gulonic acid as described in EXAMPLE 3.

EXAMPLE 2 was repeated, except that water was used as the eluant and the temperature on the jacket of the column and the water feed was controlled at 95° C. The results are displayed in FIG. 3.

EXAMPLE 5

COMPARATIVE EXAMPLE

A process similar to that described in U.S. Pat. No. 4,323,702 was employed, i.e., the acid (2-keto-L-gulonic acid) is absorbed onto a polymer and then desorbed.

100 mL of REILLEX™ HP resin was loaded into a 1" diameter column. 500 mL of a 98 g/L 2-Keto-L-gulonic acid solution was passed over the resin at a feed rate of 8 mL/min and at ambient temperature. 100 mL of deionized water was then used to wash the resin, and the column was subsequently drained giving 26 mL of void volume water. The total 626 mL of feed, rinse and drain was analyzed to have 60 g/L of 2-keto-L-gulonic acid, giving 11.5 g 2-keto-L-gulonic acid loaded onto the resin.

500 mL of anhydrous methanol was used for elution, giving a product of 22 g/L 2-keto-L-gulonic acid (or 11 g), but also containing 9.7% by weight of water.

EXAMPLE 6

2-KETO-L-GULONIC ACID PURIFICATION USING CONTINUOUS CHROMATOGRAPHY

A continuous chromatography system (AST Model C-90 CSEP; from Advanced Separation Technologies Inc., Lakeland, Fla., USA) was used to recover 2-keto-L-gulonic acid into methanol from a fermentation broth.

Figure 4:
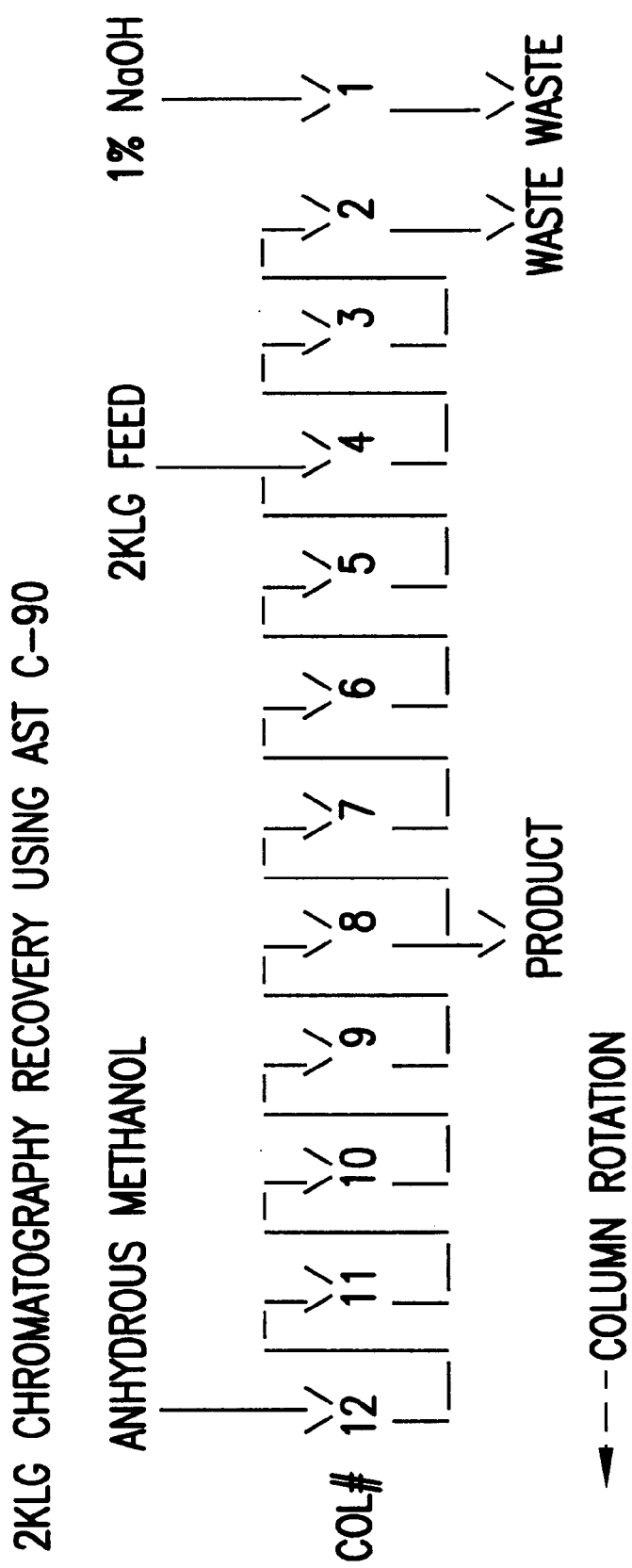
FIG. 4 is a diagram of the continuous chromatography system employed in EXAMPLE 6.

The system was piped as shown in FIG. 4. Twelve columns were loaded with 160 mL each of Reilley HP polyvinylpyridine resin and fixed to the system. These columns were rotated in a circle to the next position every 16 minutes, with a complete revolution taking 192 minutes.

Anhydrous methanol was pumped into position 12 at a rate of 31.2 mL/min, feed solution (prepared according to Example 1 above) was pumped into position 4 at a rate of 6.5 mL/min and the desired product was pumped out of position 8 at a rate of 19.8 mL/min, giving a waste flow at position 2 of 17.2 mL/min.

A 1% sodium hydroxide solution was used to continuously regenerate the resin at position 1 (flow rate 9 mL/min.) A 70° C. hot water spray on the columns was used on positions 8–12 to raise the temperature thereof.

The feed solution contained 229 g/L of 2-keto-L-gulonic acid. After one complete rotation of the continuous chromatography system, product and waste samples were taken by collecting 5 complete rotations of each. Product titer was 72 g/L of 2-keto-L-gulonic acid, 1.2% water and 88% overall purity. Waste titer from position 2 was 1.1 g/L of 2-keto-L-gulonic acid and from position 1 was 7.2 g/L of 2-keto-L-gulonic acid. Overall yield of 2-keto-L-gulonic acid from the separation was approximately 94%.

What is claimed is:

1. A process for the purification of 2-keto-L-gulonic acid using a plurality of chambers, each of said plurality of chambers containing solid particulate matter and having an inlet and an outlet, said process comprising the steps of:
    (a) introducing an aqueous solution containing 2-keto-L-gulonic acid into one of said plurality of chambers through said inlet thereof such that said aqueous solution contacts said solid particulate material therein and then exits through said outlet thereof;
    (b) introducing a solvent into said chamber through said inlet thereof such that said aqueous solution contacts said solid particulate material therein and then exits through said outlet thereof;
    (c) conducting said aqueous solution exiting said chamber through said outlet thereof to another chamber of said plurality of chambers;
    (d) collecting said solvent exiting said chamber through said outlet thereof;
    (e) introducing said aqueous solution into said another chamber of said plurality of chambers through said inlet thereof such that said aqueous solution contacts said solid particulate material therein and then exits through said outlet thereof; and
    (f) repeating steps (b)–(e) for each chamber of said plurality of chambers.

2. The process according to claim 1, wherein said solid particulate matter is a weakly basic ion exchange resin.

3. The process according to claim 2, wherein said weakly basic ion exchange resin is an anionic resin having pyridine functionality.

4. The process according to claim 3, wherein said anionic resin having pyridine functionality is a polymer comprising residues of vinylpyridine.

5. The process according to claim 1, wherein said solvent is methanol.

6. The process according to claim 1, wherein said solvent is water.

7. The process according to claim 1, wherein said aqueous solution is a fermentation broth.

8. The process according to claim 1, wherein the temperature of said solvent is increased during at least one repetition of steps (b)–(e).

9. The process according to claim 1, further comprising the step of
    (d') introducing an ionic solution into said chamber through said inlet thereof such that said ionic solution contacts said solid particulate material therein and then exits said chamber through said outlet thereof.

10. A process for the purification of 2-keto-L-gulonic acid using a plurality of chambers, each of said plurality of chambers containing solid particulate matter and having an inlet and an outlet, said process comprising the steps of:
    (a) introducing an aqueous solution containing 2-keto-L-gulonic acid into one of said plurality of chambers through said inlet thereof such that said aqueous solution contacts said solid particulate material therein and then exits through said outlet thereof;
    (b) introducing a solvent into said chamber through said inlet thereof such that said aqueous solution contacts said solid particulate material therein and then exits through said outlet thereof;
    (c) conducting said aqueous solution exiting said chamber through said outlet thereof to another chamber of said plurality of chambers;
    (d) conducting said solvent exiting said chamber through said outlet thereof to another chamber of said plurality of chambers;
    (e) introducing said aqueous solution into said another chamber of said plurality of chambers through said inlet thereof such that said aqueous solution contacts said solid particulate material therein and then exits through said outlet thereof;
    (f) introducing said solvent solution into said another chamber of said plurality of chambers through said inlet thereof such that said solvent contacts said solid particulate material therein and then exits through said outlet thereof; and
    (g) repeating steps (b)–(f) for each chamber of said plurality of chambers.

11. The process according to claim 10, wherein said solid particulate matter is a weakly basic ion exchange resin.

12. The process according to claim 11, wherein said weakly basic ion exchange resin is an anionic resin having pyridine functionality.

13. The process according to claim 12, wherein said anionic resin having pyridine functionality is a polymer comprising residues of vinylpyridine.

14. The process according to claim 10, wherein said solvent is methanol.

15. The process according to claim 10, wherein said solvent is water.

16. The process according to claim 10, wherein said aqueous solution is a fermentation broth.

17. The process according to claim 10, wherein the temperature of said solvent is increased during at least one repetition of steps (b)–(f).

18. The process according to claim 10, further comprising the step of
    (d') introducing an ionic solution into said chamber through said inlet thereof such that said ionic solution contacts said solid particulate material therein and then exits said chamber through said outlet thereof.

* * * * *